(12) United States Patent
Dutton et al.

(10) Patent No.: US 7,249,500 B2
(45) Date of Patent: Jul. 31, 2007

(54) DETERMINATION OF AMOUNT OF PROPPANT ADDED TO A FRACTURE FLUID USING A CORIOLIS FLOW METER

(75) Inventors: Robert E. Dutton, Louisville, CO (US); Christopher M. Russell, Cypress, TX (US)

(73) Assignee: Micro Motion, Inc., Boulder, CO (US)

( * ) Notice: Subject to any disclaimer, the term of this patent is extended or adjusted under 35 U.S.C. 154(b) by 9 days.

(21) Appl. No.: 10/542,119

(22) PCT Filed: Feb. 5, 2003
(Under 37 CFR 1.47)

(86) PCT No.: PCT/US03/03564

§ 371 (c)(1),
(2), (4) Date: Jul. 12, 2005

(87) PCT Pub. No.: WO2004/072621

PCT Pub. Date: Aug. 26, 2004

(65) Prior Publication Data

US 2006/0144136 A1  Jul. 6, 2006

(51) Int. Cl.
*E21B 47/10* (2006.01)
(52) U.S. Cl. .................................... 73/152.32
(58) Field of Classification Search .............. 73/152.32, 73/32 R, 32 A, 861.04
See application file for complete search history.

(56) References Cited

U.S. PATENT DOCUMENTS 4,109,524 A  8/1978  Smith
RE31,450 E  11/1983  Smith
4,491,025 A  1/1985  Smith et al.
4,953,097 A  8/1990  Crain et al.

(Continued)

FOREIGN PATENT DOCUMENTS

EP  0 253 504 A1  6/1987

(Continued)

OTHER PUBLICATIONS

Kalotay, Paul, Density and Viscosity Monitoring Systems Using Coriolis Flow Meters, IAS Transactions, Instrument Society of America, Nov. 25, 1999, pp. 303-310, vol. 38, No. 4, Pittsburgh, PA, US.

*Primary Examiner*—Hezron Williams
*Assistant Examiner*—Rodney Frank
(74) *Attorney, Agent, or Firm*—The Ollila Law Group LLC (57) ABSTRACT

A measurement system (200) is disclosed comprising a Coriolis flow meter (222) and a control system (224). A base fluid (250) is first flowed through the Coriolis flow meter. The Coriolis flow meter measures a density of the base fluid and transmits a base fluid density measurement to the control system. A proppant (252) is then added to the base fluid to create a fracture fluid (202). The fracture fluid is then flowed through the Coriolis flow meter. The Coriolis flow meter measures a density of the fracture fluid and transmits a fracture fluid density measurement to the control system. The control system determines an amount of proppant in the fracture fluid based on the base fluid density measurement, the fracture fluid density measurement, and a density of the proppant.

21 Claims, 5 Drawing Sheets

U.S. PATENT DOCUMENTS

| | | |
|---|---|---|
| 5,423,205 A | 6/1995 | Farchone |
| 6,412,354 B1 * | 7/2002 | Birchak et al. ........ 73/861.356 |
| 6,491,421 B2 * | 12/2002 | Rondeau et al. ................ 366/8 |
| 2002/0093875 A1 | 7/2002 | Rondeau et al. |

FOREIGN PATENT DOCUMENTS

| | | |
|---|---|---|
| EP | 0253504 A1 | 1/1988 |
| EP | 1109016 A2 | 6/2001 |
| RU | 2 189 577 C2 | 9/2002 |
| RU | 2 256 786 C2 | 7/2005 |
| WO | WO96/08697 | 3/1996 |

* cited by examiner

*FIG. 1*

*PRIOR ART*

FIG. 2

CONTROL SYSTEM
224

DISPLAY
302

USER I/F
304

AUX I/F
306

DETERMINATION OF AMOUNT OF PROPPANT ADDED TO A FRACTURE FLUID USING A CORIOLIS FLOW METER

BACKGROUND OF THE INVENTION

1. Field of the Invention

The invention is related to the field of measurement systems, and in particular, to a system and method that use measurements from a Coriolis flow meter to determine the amount of proppant in a fracture fluid.

2. Statement of the Problem

Oil, gas, and other resources under ground are obtained by drilling a well. The well is drilled to a certain depth and cased in cement. The well extends through multiple zones in the ground that a drilling crew may wish to tap. To tap into a certain zone, the drilling crew fractures a portion of the casing in the desired zone. The fracturing process used could be hydraulic fracturing, pneumatic fracturing, or another type of fracturing. With the casing fractured, the drilling crew then pumps a fracture fluid into the fracture to keep the fracture open. The fracture fluid holds the fracture open while still being permeable. This enables the oil and gas to more easily flow through the fracture into the well-bore.

The fracture fluid is made up of a base fluid and a proppant. To make the base fluid, a Guar gum is added to water in a large tank. A mixer within the tank continually mixes the Guar gum and the water together to make the base fluid. When mixed, the base fluid has the consistency somewhat like molasses.

A proppant, such as sand, is then added to the base fluid in the tank to make the fracture fluid. The amount of sand added depends on soil type, soil conditions, and other factors. The mixer in the tank mixes the base fluid and the sand together to make the fracture fluid. The fracture fluid is then pumped into the well-bore to help keep the fracture open. The amount of the sand in the fracture fluid determines how well the fracture fluid is able to hold the fracture open.

Because the amount of sand in the fracture fluid is important, the drilling crew may want to measure the amount of sand added. This can be a difficult process because the fracture fluid is usually not made in a batch, but is continuously mixed. To determine the amount of sand in the fracture fluid, the drilling crew uses a nuclear densitometer to measure the density of the fracture fluid being pumped into the well-bore. A controller receives the density measurement from the nuclear densitometer and calculates the amount of sand added to the fracture fluid. The drilling crew can then adjust the amount of sand to a desired level. An example of a system for providing the fracture fluid is described below and illustrated in FIG. 1.

Unfortunately, there are problems associated with using nuclear densitometers. For instance, interstate and international transport of nuclear densitometers can be a difficult process considering the laws and regulations surrounding nuclear technology. There are also concerns for safe handling and transporting of the nuclear densitometers. The operators of the nuclear densitometers have to be certified or licensed by the proper regulatory agency. Such factors make nuclear densitometers undesirable to use.

Coriolis flow meters are used to measure the mass flow rate, density, and other information for fluids. Exemplary Coriolis flow meters are disclosed in U.S. Pat. No. 4,109,524 of Aug. 29, 1978, U.S. Pat. No. 4,491,025 of Jan. 1, 1985, and Re. 31,450 of Feb. 11, 1982, all to J. E. Smith et al. Coriolis flow meters are comprised of one or more flow tubes of a straight or curved configuration. Each flow tube configuration in a Coriolis flow meter has a set of natural modes of vibration, which may be of a simple bending, twisting, torsional, or coupled type. Each flow tube is driven to oscillate at resonance in one of these natural modes of vibration. Fluid flows into the flow meter from a connected pipeline on the inlet side of the flow meter. The fluid is directed through the flow tube(s), and exits the flow meter through the outlet side of the flow meter. The natural vibration modes of the vibrating, fluid-filled system are defined in part by the combined mass of the flow tubes and the mass of the fluid flowing through the flow tubes.

As fluid begins to flow through the flow tubes, Coriolis forces cause points along the flow tubes to have a different phase. The phase on the inlet side of the flow tube commonly lags the driver while the phase on the outlet side of the flow tube leads the driver. Pickoffs are affixed to the flow tube(s) to measure the motion of the flow tube(s) and generate pickoff signals that are representative of the motion of the flow tube(s).

Meter electronics, or any other ancillary electronics or circuitry connected to the flow meter, receive the pickoff signals. The meter electronics processes the pickoff signals to determine the phase difference between the pickoff signals. The phase difference between two pickoff signals is proportional to the mass flow rate of the fluid through the flow tube(s). The meter electronics can also process one or both of the pickoff signals to determine the density of the fluid.

Unfortunately, Coriolis flow meters have not been used to measure the density of a fracture fluid. First, the fracture fluid is usually pumped down the well-bore through a large tube, such as an eight inch tube. Coriolis flow meters have not been built large enough to measure an eight inch stream. Secondly, most Coriolis flow meters have curved flow tubes. The erosive properties of sand through the curved flow tubes prevents the curved-tube Coriolis flow meter from being a viable option. The sand would damage the flow tubes in a matter of hours. For these reasons, Coriolis flow meters have not been used to measure the fracture fluid, and nuclear densitometers continue to be used.

SUMMARY OF THE SOLUTION

The invention helps solve the above problems with a measurement system comprising a Coriolis flow meter and a control system. A base fluid is first flowed through the Coriolis flow meter. The Coriolis flow meter measures a density of the base fluid and transmits a base fluid density measurement to the control system. A proppant is added to the base fluid creating a fracture fluid. The fracture fluid is then flowed through the Coriolis flow meter. The Coriolis flow meter measures a density of the fracture fluid and transmits a fracture fluid density measurement to the control system. The control system determines an amount of proppant in the fracture fluid based on the base fluid density measurement, the fracture fluid density measurement, and a density of the proppant.

The measurement system advantageously replaces nuclear technology with Coriolis technology. Coriolis flow meters can provide accurate density measurements, while avoiding the problems of handling and transporting radioactive sources and instruments. Coriolis flow meters also do not have the intrinsic safety concerns of the nuclear densitometer.

In another example of the invention, the Coriolis flow meter is configured to receive a slip stream of material. To provide the slip stream, the measurement system further comprises a first tube and a second tube. The first tube has a first end configured to connect to an input of the Coriolis flow meter and has a second end configured to connect to a discharge of a tank. The second tube has a first end configured to connect to an output of the Coriolis flow meter and has a second end configured to connect to a tank. The first tube receives a slip stream of material from the discharge of the tank. The slip stream travels through said first tube, through said Coriolis flow meter, through said second tube, and back into said tank. The slip stream advantageously provides a smaller flow to measure, such as a one inch flow.

Other examples of the invention may be disclosed below.

The following sets forth aspects of the invention. One aspect of the invention comprises a measurement system comprising a Coriolis flow meter and a control system, said measurement system characterized by:

said Coriolis flow meter being configured to measure a density of a base fluid (250) flowing through said Coriolis flow meter to generate a base fluid density measurement, transmit said base fluid density measurement, measure a density of a fracture fluid (202) flowing through said Coriolis flow meter to generate a fracture fluid density measurement, wherein said fracture fluid comprises a mixture of said base fluid and a proppant (252), and transmit said fracture fluid density measurement; and said control system being configured to receive said base fluid density measurement and said fracture fluid density measurement, and determine an amount of said proppant in said fracture fluid based on said base fluid density measurement, said fracture fluid density measurement, and a density of said proppant.

Preferably, the Coriolis flow meter comprises a straight tube Coriolis flow meter.

Preferably, the Coriolis flow meter is configured to receive a slip stream of said fracture fluid to measure said density of said fracture fluid.

Preferably, the measurement system further comprises:

a first tube having a first end configured to connect to an input of said Coriolis flow meter and having a second end configured to connect to a discharge of a tank; and a second tube having a first end configured to connect to an output of said Coriolis flow meter and having a second end configured to connect to said tank;

wherein said first tube is configured to receive a slip stream of material from said discharge of said tank, said slip stream travels through said first tube, through said Coriolis flow meter, through said second tube, and back into said tank.

Preferably, the control system is configured to determine said density of said proppant.

Preferably, the control system comprises a display system configured to provide said amount of said proppant to a user.

Preferably, the control system comprises an auxiliary interface configured to transmit a signal representing said amount of said proppant to an auxiliary system.

Preferably, the control system comprises a user interface configured to receive said density of said proppant entered by a user.

Preferably, the control system is configured to:

calculate a velocity of said fracture fluid;

determine if said velocity of said fracture fluid exceeds a threshold; and provide an indication if said velocity of said fracture fluid exceeds said threshold.

Preferably, the control system is configured to:

calculate an average density of said base fluid based on a plurality of density measurements of said base fluid by said Coriolis flow meter; and determine said amount of said proppant in said fracture fluid based on said average density of said base fluid, said fracture fluid density measurement, and said density of said proppant.

Preferably, the Coriolis flow meter is configured to measure a mass flow rate of said fracture fluid, and provide at least one of said mass flow rate of said fracture fluid and a drive gain of said Coriolis flow meter to said control system; and said control system is configured to provide at least one of said mass flow rate of said fracture fluid and said drive gain of said Coriolis flow meter to a user.

Another aspect of the invention comprises a method of measuring an amount of proppant in a fracture fluid, said method comprising the step of:

determining a density of said proppant;

said method characterized by the steps of:

measuring a density of a base fluid with a Coriolis flow meter to generate a base fluid density measurement;

measuring a density of a fracture fluid with said Coriolis flow meter to generate a fracture fluid density measurement, wherein said fracture fluid comprises a mixture of said base fluid and a proppant; and determining an amount of said proppant in said fracture fluid based on said base fluid density measurement, said fracture fluid density measurement, and said density of said proppant.

Preferably, the step of measuring a density of a fracture fluid with said Coriolis flow meter comprises:

measuring said density of said fracture fluid with a straight tube Coriolis flow meter.

Preferably, the step of measuring a density of a fracture fluid with said Coriolis flow meter comprises:

receiving a slip stream of said fracture fluid into said Coriolis flow meter to measure said density of said fracture fluid.

Preferably, the method further comprises the steps of:

connecting a first end of a first tube to an input of said Coriolis flow meter;

connecting a second end of said first tube to a discharge of a tank;

connecting a first end of a second tube to an output of said Coriolis flow meter; and connecting a second end of said second tube to said tank;

wherein said first tube receives a slip stream of material from said discharge of said tank, said slip stream travels through said first tube, through said Coriolis flow meter, through said second tube, and back into said tank.

Preferably, the method further comprises the step of providing said amount of said proppant to a user.

Preferably, the method further comprises the step of transmitting a signal representing said amount of said proppant to an auxiliary system.

Preferably, the method further comprises the step of receiving said density of said proppant from a user.

Preferably, the method further comprises the steps of:

calculating a velocity of said fracture fluid;

determining if said velocity of said fracture fluid exceeds a threshold; and providing an indication if said velocity of said fracture fluid exceeds said threshold.

Preferably, the method further comprises the steps of:

calculating an average density of said base fluid based on a plurality of density measurements of said base fluid by said Coriolis flow meter; and determining said amount of said proppant in said fracture fluid based on said average density of said base fluid, said fracture fluid density measurement, and said density of said proppant.

Preferably, the method further comprises the steps of:

measuring a mass flow rate of said fracture fluid with said Coriolis flow meter; and providing at least one of said mass flow rate of said fracture fluid and a drive gain of said Coriolis flow meter to a user.

DESCRIPTION OF THE DRAWINGS

The same reference number represents the same element on all drawings.

DETAILED DESCRIPTION OF THE INVENTION

Figure 1:
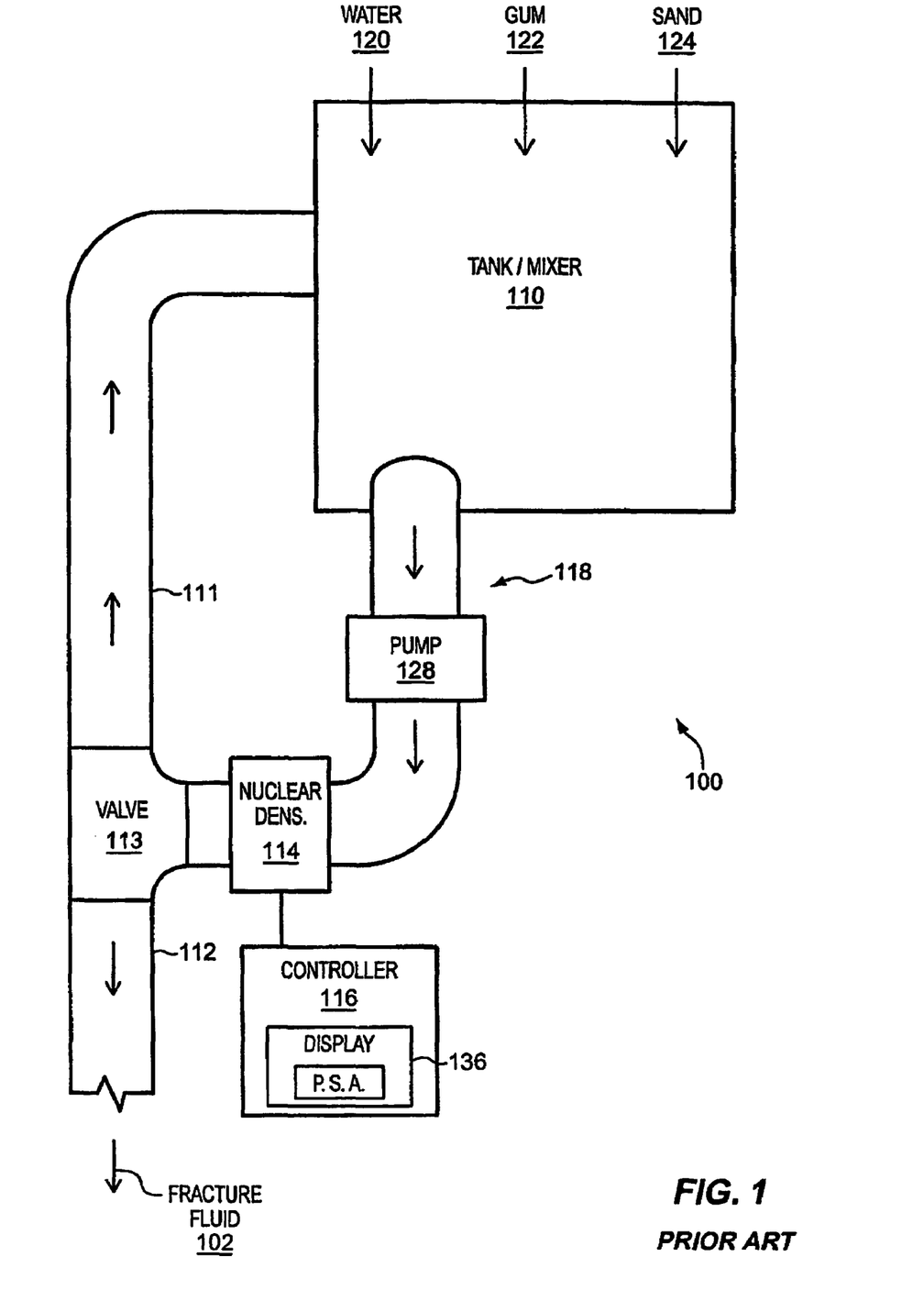
FIG. 1 illustrates a system for supplying a fracture fluid to a well-bore in the prior art.

FIG. 1 illustrates a system for supplying a fracture fluid to a well-bore in the prior art to assist in understanding the invention. FIGS. 2-5 and the following description depict specific examples of the invention to teach those skilled in the art how to make and use the best mode of the invention. For the purpose of teaching inventive principles, some conventional aspects of the invention have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

System for Supplying a Fracture Fluid in the Prior Art—FIG. 1

FIG. 1 illustrates a fracture fluid system 100 for supplying a fracture fluid 102 to a well-bore in the prior art. Fracture fluid system 100 is comprised of a tank/mixer 110, a recirculation tube 111, a supply tube 112, a discharge tube 118, a valve 113, a pump 128, a nuclear densitometer 114, and a controller 116. Discharge tube 118 is connected to tank/mixer 110 at one end and valve 113 at the other. Pump 128 and nuclear densitometer 114 are connected to discharge tube 118. Recirculation tube 111 is connected to valve 113 at one end and tank/mixer 110 at the other. Supply tube 112 is connected to valve 113 and is configured to transport the fracture fluid 102 to the well-bore. Valve 113 either directs a flow of the fracture fluid 102 through recirculation tube 111 or through supply tube 112. Supply tube 112, recirculation tube 111, and discharge tube 118 have at least eight inch diameters. Controller 116 is coupled to nuclear densitometer 114.

In operation, water 120, gum 122, and sand 124 are added to tank/mixer 110. Tank/mixer 110 mixes the water 120, the gum 122, and the sand 124 together to make the fracture fluid 102. The amount of sand added to the water 120 and the gum 122 in the fracture fluid 102 depends on the soil type, soil conditions, and other factors. The operator of fracture fluid system 100 uses nuclear densitometer 114 and controller 116 to measure the amount of sand in the fracture fluid 102.

As the full stream of the fracture fluid 102 flows through discharge tube 118, nuclear densitometer 114 measures the density of the fracture fluid 102. Nuclear densitometer 114 transmits the density measurement to controller 116. Controller 116 knows the density of the sand 124, the density of the water 120, and the density of the gum 122. These values may be entered into controller 116 by the operator. Controller 116 calculates the amount of sand in the fracture fluid 102 based on the density measurement of the fracture fluid 102, and the known densities of the sand 124, the water 120, and the gum 122. Controller 116 includes a display 136. Controller 116 provides the amount of sand in the fracture fluid 102 to the operator using display 136.

As described above, there are many problems associated with using nuclear densitometer 114. For instance, interstate and international transport of nuclear densitometers can be a difficult process, safe handling and transporting of the nuclear densitometers is a concern, and the people operating the nuclear densitometers have to be certified or licensed by the proper regulatory agency. Such factors make nuclear densitometers undesirable to use.

Figure 2:
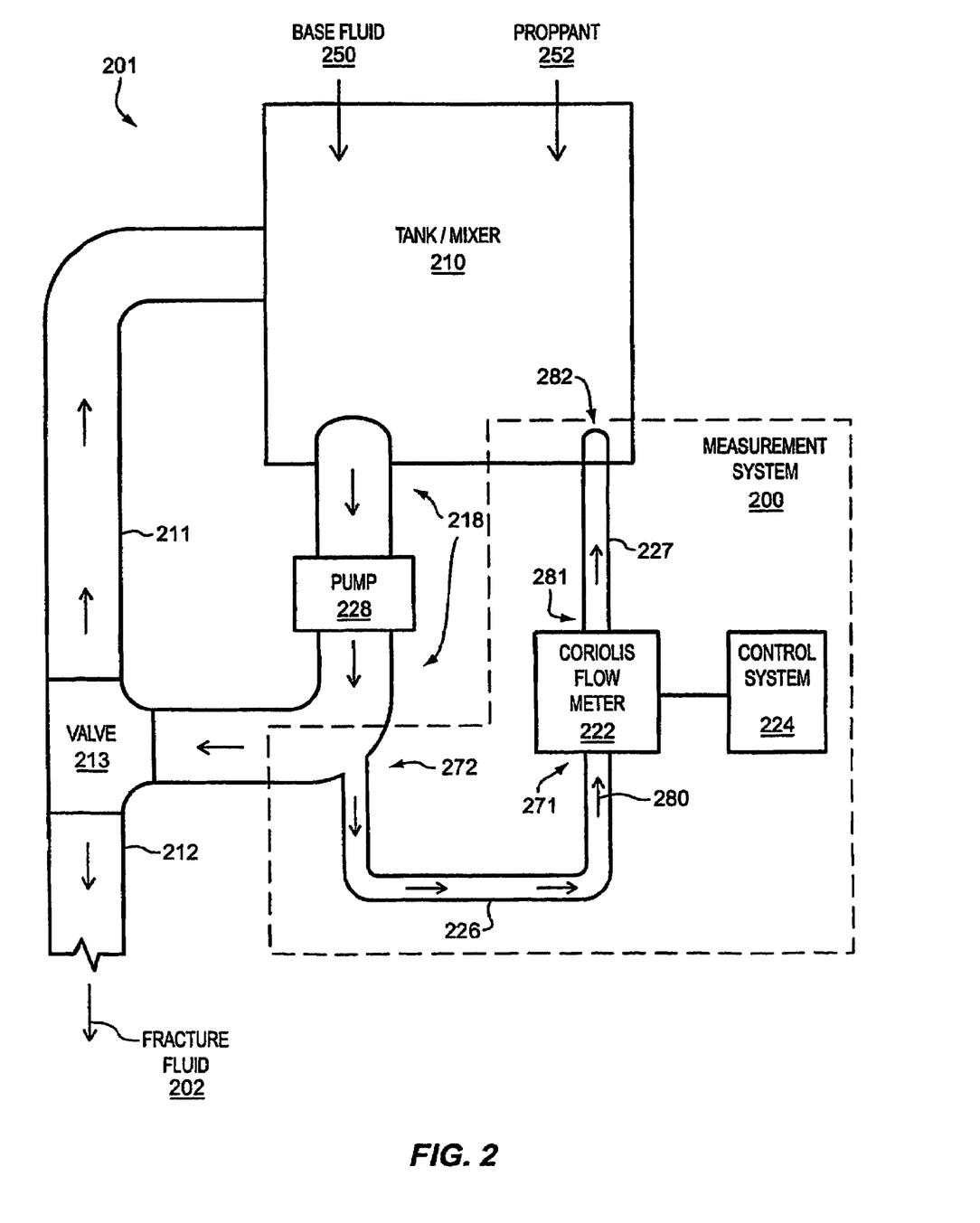
FIG. 2 illustrates a measurement system in an example of the invention.

Measurement System and Operation—FIG. 2

FIG. 2 illustrates a measurement system 200 in an example of the invention. Measurement system 200 is configured to operate with a fracture fluid system 201 for supplying a fracture fluid 202 to a well-bore (not shown). Fracture fluid system 201 is comprised of a tank/mixer 210, a discharge tube 218, a valve 213, a recirculation tube 211, a supply tube 212, a pump 228, and measurement system 200. Discharge tube 218 is connected to tank/mixer 210 at one end and valve 213 at the other. Pump 228 is also connected to discharge tube 218. Recirculation tube 211 is connected to valve 213 at one end and tank/mixer 210 at the other. Supply tube 212 is connected to valve 213 and is configured to transport the fracture fluid 202 to the well-bore. Valve 213 either directs a flow of material through recirculation tube 211 or through supply tube 212. Fracture fluid system 201 may be comprised of many other components that are not shown for the sake of brevity.

Measurement system 200 is comprised of a Coriolis flow meter 222 and a control system 224. Measurement system 200 may also include tubes 226-227 that form a slip stream from discharge tube 218. Tubes 226-227 may be one inch rubber tubing. Tube 226 includes ends 271 and 272. End 271 connects to an inlet end of Coriolis flow meter 222. End 272 connects to discharge tube 218. End 272 may connect to an elbow of discharge tube 218 to obtain the best results. Tube 227 includes ends 281 and 282. End 281 connects to an outlet end of Coriolis flow meter 222 and end 282 connects to tank/mixer 210. Tube 226, Coriolis flow meter 222, and tube 227 are configured to receive a slip stream 280 of material. The slip stream 280 enters tube 226, and passes through tube 226, through Coriolis flow meter 222, through tube 227, and back into tank/mixer 210.

The following definitions may be helpful in understanding the invention. A Coriolis flow meter comprises any meter configured to measure a density of a material based on the Coriolis principle. An example of a Coriolis flow meter is a Model T-100 straight tube meter manufactured by Micro Motion Inc. of Boulder, Colo. A fracture fluid comprises any fluid, material, or mixture used to resist crushing of a fracture in a well-bore and provide a permeable path. A proppant comprises any material or agent used in a fracture fluid to help keep the fractures open. An example of a proppant is sand. A base fluid comprises any material or agent mixed with a proppant to form a fracture fluid. A tank or tank/mixer comprises any tub or container that stores a material. A tube comprises any hose, tubing, line, pipe, etc.

In operation, tank/mixer 210 receives and mixes the base fluid 250. Based on the setting of valve 213, pump 228 circulates the base fluid 250 through discharge tube 218 and recirculation tube 211. Tube 226 receives a slip stream 280 of the base fluid 250. The slip stream 280 of the base fluid 250 travels through tube 226, through Coriolis flow meter 222, through tube 227, and back into tank/mixer 210. With the base fluid 250 flowing through Coriolis flow meter 222, Coriolis flow meter 222 measures a density of the base fluid 250. Coriolis flow meter 222 transmits a base fluid density measurement to control system 224.

Tank/mixer 210 then receives and mixes the proppant 252 with the base fluid 250 to make the fracture fluid 202. Based on the setting of valve 213, pump 228 circulates the fracture fluid 202 through discharge tube 218 and recirculation tube 211. Tube 226 receives a slip stream 280 of the fracture fluid 202. The slip stream 280 of the fracture fluid 202 travels through tube 226, through Coriolis flow meter 222, through tube 227, and back into tank/mixer 210. With the fracture fluid 202 flowing through Coriolis flow meter 222, Coriolis flow meter 222 measures a density of the fracture fluid 202. Coriolis flow meter 222 transmits a fracture fluid density measurement to control system 224.

Control system 224 receives the base fluid density measurement and the fracture fluid density measurement. Control system 224 also receives the density of the proppant 252. Control system 224 may receive the density of the proppant 252 from an operator, from a memory, or from another source. Control system 224 determines an amount of the proppant 252 in the fracture fluid 202 based on the base fluid density measurement, the fracture fluid density measurement, and the density of the proppant 252. An operator of fracture fluid system 201 can look at the amount of proppant 252 in the fracture fluid 202, as determined by control system 224, to adjust the amount of the proppant 252 added to the fracture fluid 202. Based on this disclosure, those skilled in the art will appreciate how to modify existing measurement systems to make measurement system 200.

When the fracture fluid 202 has the proper amount of proppant 252, valve 213 is switched so that the fracture fluid 202 is pumped down hole through supply tube 212. There maybe other devices or systems connected to supply tube 212 to pump the fracture fluid 202 down hole, such as a large pump.

Figure 3:
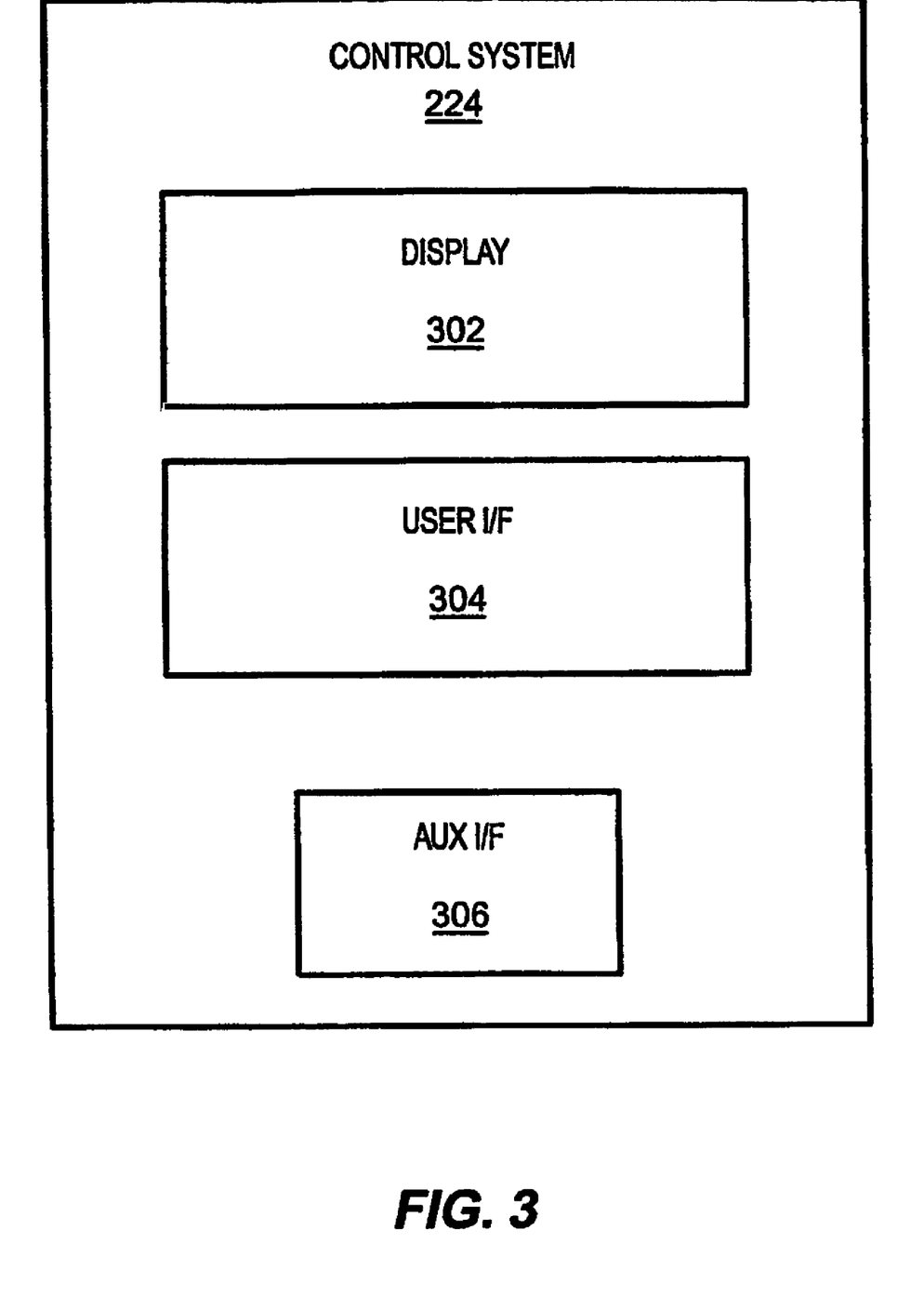
FIG. 3 illustrates an example of a control system in an example of the invention.

Control System—FIG. 3

FIG. 3 illustrates an example of control system 224 in an example of the invention. Control system 224 comprises a display 302, a user interface 304, and an auxiliary interface 306. An example of control system 224 is the Daniel™ FloBoss™ 407. Display 302 is configured to display any relevant data to an operator. An example of display 302 is a Liquid Crystal Display (LCD). User interface 304 is configured to allow the operator to enter information into control system 224. An example of user interface 304 is a keypad. Auxiliary interface 306 is configured to transmit information to, and receive information from, an auxiliary system (not shown). An example of auxiliary interface 306 is a serial data port.

Control system 224 may also comprise a processor and a storage media. The operation of control system 224 may be controlled by instructions that are stored on the storage media. The instructions can be retrieved and executed by the processor. Some examples of instructions are software, program code, and firmware. Some examples of storage media are memory devices, tape, disks, integrated circuits, and servers. The instructions are operational when executed by the processor to direct the processor to operate in accord with the invention. The term "processor" refers to a single processing device or a group of inter-operational processing devices. Some examples of processors are computers, integrated circuits, and logic circuitry. Those skilled in the art are familiar with instructions, processors, and storage media Coriolis Flow Meter—FIG. 4

Figure 4:
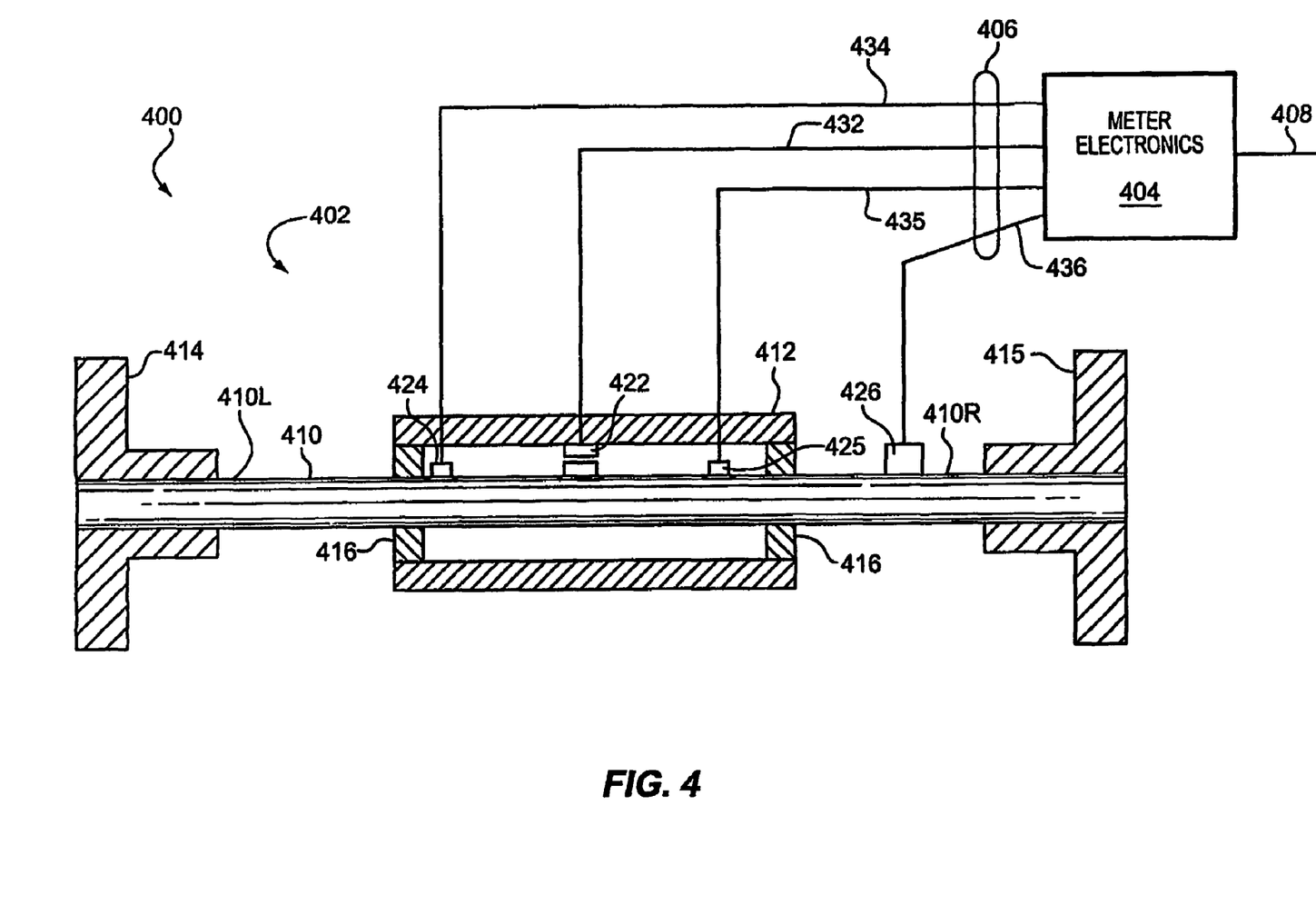
FIG. 4 illustrates an example of a Coriolis flow meter in an example of the invention.

FIG. 4 illustrates an example of a Coriolis flow meter 400 in an example of the invention. Coriolis flow meter 400 could be Coriolis flow meter 222 illustrated in FIG. 2. Coriolis flow meter 400 comprises a Coriolis sensor 402 and meter electronics 404. Meter electronics 404 is connected to Coriolis sensor 402 via paths 406. Meter electronics 404 is configured to provide density, mass flow rate, volumetric flow rate, totalized mass flow, and other information over path 408.

Coriolis sensor 402 comprises a flow tube 410, a balance bar 412, process connections 414-415, a driver 422, pickoffs 424-425, and a temperature sensor 426. Flow tube 410 includes a left end portion designated 410L and a right end portion designated 41 OR. Flow tube 410 and its ends portions 410L and 410R extend the entire length of Coriolis sensor 402 from an input end of flow tube 410 to an output end of flow tube 410. Balance bar 412 is connected at its ends to flow tube 410 by brace bar 416.

Left end portion 410L is affixed to inlet process connection 414. Right end portion 410R is affixed to outlet process connection 415. Inlet process connection 414 and outlet process connection 415 are configured to connect Coriolis sensor 402 to a pipeline (not shown).

In a conventional manner, driver 422, left pickoff 424, and right pickoff 425 are coupled to flow tube 410 and balance bar 412. Meter electronics 404 transmits a driver signal to driver 422 over path 432. Responsive to the driver signal, driver 422 vibrates flow tube 410 and balance bar 412 in phase opposition at the resonant frequency of the fluid-filled flow tube 410. The oscillation of vibrating flow tube 410 induces Coriolis deflections in the flow tube 410 in a well known manner. The pickoffs 424 and 425 detect the Coriolis deflections and transmit pickoff signals that represent the Coriolis deflections over paths 434 and 435, respectively.

Temperature sensor 426 is connected to flow tube 410. Temperature sensor 426 detects the temperature of the fluid flowing through flow tube 410. Temperature sensor 426 generates a temperature signal, and transmits the temperature signal to meter electronics 404 over path 436.

Figure 5:
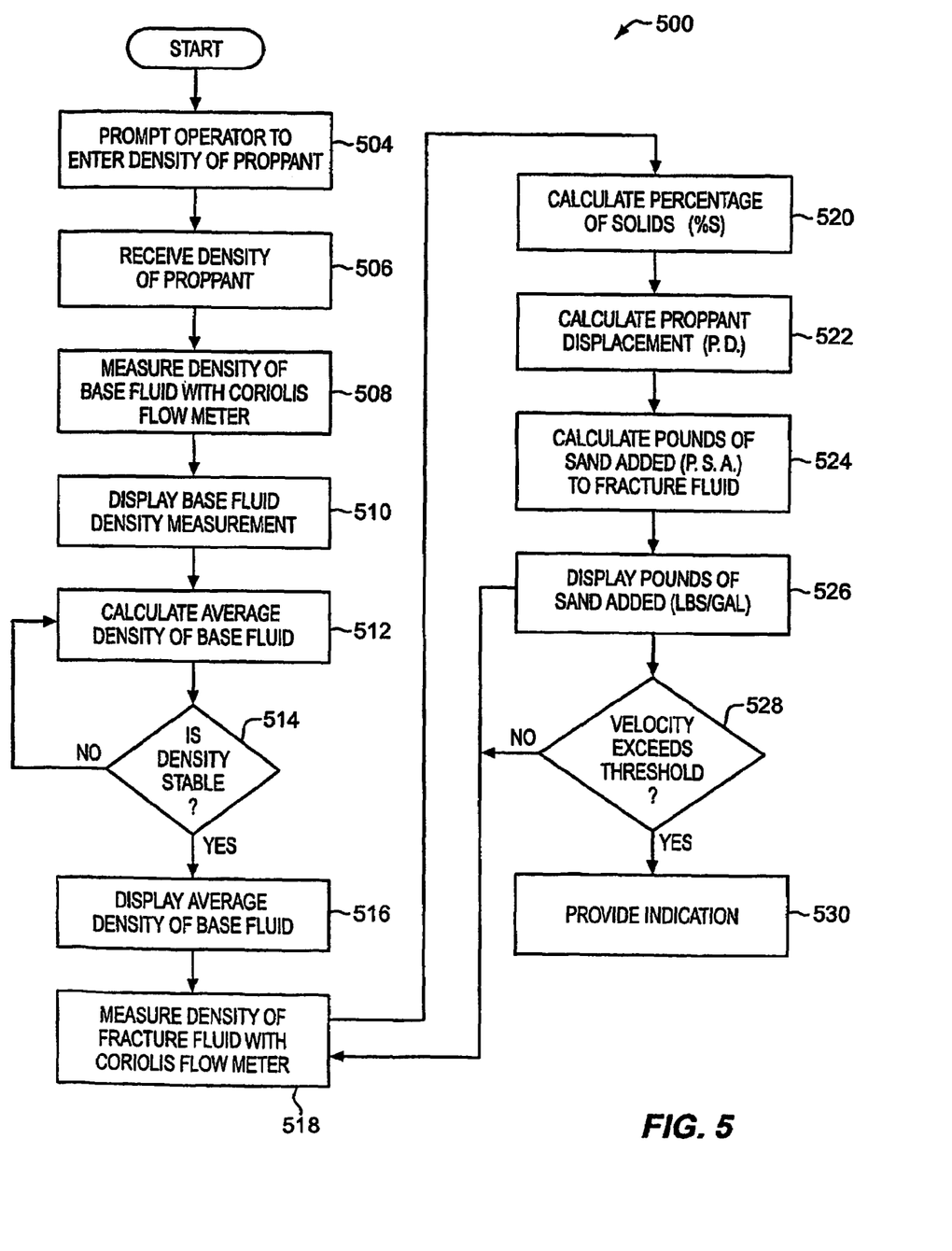
FIG. 5 is a flow chart illustrating an example operation of a measurement system in an example of the invention.

Example Operation of Measurement System—FIG. 5

FIG. 5 is a flow chart illustrating an example method 500 of operation of measurement system 200 in an example of the invention. An operator turns on control system 224 and Coriolis flow meter 222. Control system 224 receives an instruction to clear the memory on control system 224. The operator clears the memory by entering a "Clear" instruction through user interface 304. In step 504, control system 224 prompts the operator to enter a density of the proppant 252. Control system 224 prompts the operator by displaying "Enter Density of Proppant" through display 302. The operator enters the density of the proppant 252, in pounds per gallon, through user interface 304. Assume for this example that the proppant 252 is sand having a density of 22.1 lbs/gal. In step 506, control system 224 receives the density of the proppant 252 as entered by the operator. The density of the proppant may also be retrieved from memory, or received from another system.

Tank/mixer 210 mixes the base fluid 250 without the proppant 252. Based on the setting of valve 213, pump 228 circulates the base fluid 250 through discharge tube 218 and recirculation tube 211. Tube 226 receives a slip stream 280 of the base fluid 250. The slip stream 280 of the base fluid 250 travels through tube 226, through Coriolis flow meter 222, through tube 227, and back into tank/mixer 210. With the base fluid 250 flowing through Coriolis flow meter 222, Coriolis flow meter 222 measures a density of the base fluid 250 in step 508. Coriolis flow meter 222 transmits a base fluid density measurement to control system 224. Control system 224 displays the base fluid density measurement to the operator in step 510. Coriolis flow meter 222 may also measure a mass flow rate of the base fluid 250, a temperature of the base fluid 250, and other parameters in step 508. Control system 224 may also display the mass flow rate, the temperature, and the other parameters to the operator in step 510. The operator could scroll through the different parameters to view a desired parameter.

In step 512, control system 224 calculates an average density of the base fluid 250. Control system 224 calculates the average density by taking the average of ten density measurements of the base fluid 250. Control system 224 may also calculate the average density by taking the average of the density measurements over a five second interval. While calculating the average density, control system 224 may display "Stabilizing on Base Fluid" to the operator. Control system 224 may calculate the average density responsive to an instruction from the operator. For instance, the operator watches the density measurement and the temperature measurement displayed by control system 224 to see if the measurements stabilize. If the measurements stabilize, then the operator instructs control system 224 to calculate the average density.

In step 514, control system 224 determines whether the average density just calculated is stable. For instance, if the average density varied by more than 1% within a five second interval, then the average density is not stable. In that case, control system 224 displays "Unstable Density" to the operator and returns to step 512. If the average density did not vary by more than 1%, then the average density is stable and can be used. Control system 224 displays the stable average density of the base fluid 250 to the operator in step 516.

At this point, tank/mixer 210 mixes the proppant 252 into the base fluid 250 to make the fracture fluid 202. Based on the setting of valve 213, pump 228 circulates the fracture fluid 202 through discharge tube 218 and recirculation tube 211. Pump 228 re-circulates the fracture fluid to continuously blend the fracture fluid 202 to the proper specifications. Tube 226 receives a slip stream 280 of the fracture fluid 202. The slip stream 280 of the fracture fluid 202 travels through tube 226, through Coriolis flow meter 222, through tube 227, and back into tank/mixer 210. With the fracture fluid 202 flowing through Coriolis flow meter 222, Coriolis flow meter 222 measures a density of the fracture fluid 202 in step 518. Coriolis flow meter 222 transmits a fracture fluid density measurement to control system 224.

Control system 224 then calculates the pounds of sand added to the fracture fluid 202. To calculate the pounds of sand added, control system 224 uses the following equations. In step 520, control system 224 calculates the percentage of solids (%S) in the fracture fluid 202 using equation 1.

$$\% S = (\rho_{frac\ fluid} - \rho_{base\ fluid})/(\rho_{proppant} - \rho_{base\ fluid}) \quad [1]$$

where $\rho_{frac\ fluid}$ is the density of the fracture fluid 202, $\rho_{base\ fluid}$ is the density of the base fluid 250, and $\rho_{proppant}$ is the density of the proppant 252.

In step 522, control system 224 calculates the proppant displacement (P.D.) using equation 2.

$$P.D. = 231/\rho_{proppant} \quad [2]$$

where $\rho_{proppant}$ is the density of the proppant 252.

In step 524, control system 224 calculates the pounds of sand added (P.S.A.) to the fracture fluid 202 using equation 3.

$$P.S.A. = (\%S * 231)/((1 - \%S) * P.D.) \quad [3]$$

The pounds of sand added (P.S.A.) may also be referred to as pounds of proppant added (P.P.A.).

Control system 224 may calculate the pounds of sand added using equation 4 instead of equations 1-3.

$$P.S.A. = (\rho_{frac\ fluid} - \rho_{base\ fluid})/((1 - (\rho_{frac\ fluid}/\rho_{proppant}))) \quad [4]$$

where $\rho_{frac\ fluid}$ is the density of the fracture fluid 202, $\rho_{base\ fluid}$ is the density of the base fluid 250, and $\rho_{proppant}$ is the density of the proppant 252.

In step 526, control system 224 displays the pounds of sand added to the fracture fluid 202. Control system 224 displays the pounds of sand added in units of pounds of sand added per one gallon of water. Control system 224 also generates a signal representing the pounds of sand added. The signal may be a 4-20 mA signal for an auxiliary system (not shown). Coriolis flow meter 222 may also measure a mass flow rate of the fracture fluid 202, a temperature of the fracture fluid 202, and other parameters in step 518. Control system 224 may display the mass flow rate, the temperature, and the other parameters to the operator in step 526. The operator could scroll through the different parameters to view a desired parameter. Control system 224 returns to step 518.

Method 500 may further include steps 528 and 530. In step 528, control system 224 compares the velocity of the fracture fluid 202 to a threshold value. Control system 224 calculates the velocity (velocity $_{material}$) of the fracture fluid 202 using equation 5.

$$velocity_{material} = flow\ rate_{material} * A.F. \quad [5]$$

where A.F. is an area factor and flow rate $_{material}$ is the flow rate of the material. The area factor (A.F.) may be received from the operator or retrieved from a memory or other system. If the velocity of the fracture fluid 202 exceeds the threshold value, then control system 224 provides an indication that the velocity exceeds the threshold value in step 530. For instance, if the velocity of the fracture fluid 202 exceeds 12 ft/sec, then control system 224 triggers an alarm. If the velocity of the fracture fluid 202 does not exceed the threshold value, then control system 224 returns to step 518.

Control system 224 continues to calculate the pounds of sand added to the fracture fluid 202. Tank/mixer 210 is a continuous mixing system, not a batch system. Therefore, the operator has control system 224 measure the pounds of sand added as long as tank/mixer 210 is providing the fracture fluid 202 to the well-bore.

What is claimed is:

1. A measurement system comprising a Coriolis flow meter and a control system, said measurement system characterized by:

said Coriolis flow meter being configured to measure a density of a base fluid flowing through said Coriolis flow meter to generate a base fluid density measurement, transmit said base fluid density measurement, measure a density of a fracture fluid flowing through said Coriolis flow meter to generate a fracture fluid density measurement, wherein said fracture fluid comprises a mixture of said base fluid and a proppant, and transmit said fracture fluid density measurement; and said control system being configured to receive said base fluid density measurement and said fracture fluid density measurement, and determine an amount of said proppant in said fracture fluid based on said base fluid density measurement, said fracture fluid density measurement, and a density of said proppant.

2. The measurement system of claim 1 wherein said Coriolis flow meter comprises a straight tube Coriolis flow meter.

3. The measurement system of claim 1 wherein said Coriolis flow meter is configured to receive a slip stream of said fracture fluid to measure said density of said fracture fluid.

4. The measurement system of claim 1 further comprising:

a first tube having a first end configured to connect to an input of said Coriolis flow meter and having a second end configured to connect to a discharge of a tank; and a second tube having a first end configured to connect to an output of said Coriolis flow meter and having a second end configured to connect to said tank;

wherein said first tube is configured to receive a slip stream of material from said discharge of said tank, said slip stream travels through said first tube, through said Coriolis flow meter, through said second tube, and back into said tank.

5. The measurement system of claim 1 wherein said control system is configured to determine said density of said proppant.

6. The measurement system of claim 1 wherein said control system comprises:

a display system configured to provide said amount of said proppant to a user.

7. The measurement system of claim 1 wherein said control system comprises:

an auxiliary interface configured to transmit a signal representing said amount of said proppant to an auxiliary system.

8. The measurement system of claim 1 wherein said control system comprises:

a user interface configured to receive said density of said proppant entered by a user.

9. The measurement system of claim 1 wherein said control system is configured to:

calculate a velocity of said fracture fluid;

determine if said velocity of said fracture fluid exceeds a threshold; and provide an indication if said velocity of said fracture fluid exceeds said threshold.

10. The measurement system of claim 1 wherein said control system is configured to:

calculate an avenge density of said base fluid based on a plurality of density measurements of said base fluid by said Coriolis flow meter; and determine said amount of said proppant in said fracture fluid based on said average density of said base fluid, said fracture fluid density measurement, and said density of said proppant.

11. The measurement system of claim 1 wherein:

said Coriolis flow meter is configured to measure a mass flow rate of said fracture fluid, and provide at least one of said mass flow rate of said fracture fluid and a drive gain of said Coriolis flow meter to said control system; and said control system is configured to provide at least one of said mass flow rate of said fracture fluid and said drive gain of said Coriolis flow meter to a user.

12. A method of measuring an amount of proppant in a fracture fluid, said method comprising the step of:

determining a density of said proppant;

said method characterized by the steps of:

measuring a density of a base fluid with a Coriolis flow meter to generate a base fluid density measurement;

measuring a density of a fracture fluid with said Coriolis flow meter to generate a fracture fluid density measurement, wherein said fracture fluid comprises a mixture of said base fluid and a proppant; and determining an amount of said proppant in said fracture fluid based on said base fluid density measurement, said fracture fluid density measurement, and said density of said proppant.

13. The method of claim 12 wherein the step of measuring a density of a fracture fluid with said Coriolis flow meter comprises:

measuring said density of said fracture fluid with a straight tube Coriolis flow meter.

14. The method of claim 12 wherein the step of measuring a density of a fracture fluid with said Coriolis flow meter comprises:

receiving a slip stream of said fracture fluid into said Coriolis flow meter to measure said density of said fracture fluid.

15. The method of claim 12 further comprising the steps of:

connecting a first end of a first tube to an input of said Coriolis flow meter;

connecting a second end of said first tube to a discharge of a tank;

connecting a first end of a second tube to an output of said Coriolis flow meter; and connecting a second end of said second tube to said tank;

wherein said first tube receives a slip stream of material from said discharge of said tank, said slip stream travels through said first tube, through said Coriolis flow meter, through said second tube, and back into said tank.

16. The method of claim 12 further comprising the step of:

providing said amount of said proppant to a user.

17. The method of claim 12 further comprising the step of:

transmitting a signal representing said amount of said proppant to an auxiliary system.

18. The method of claim 12 further comprising the step of:
receiving said density of said proppant from a user.

19. The method of claim 12 further comprising the steps of:
calculating a velocity of said fracture fluid;
determining if said velocity of said fracture fluid exceeds a threshold; and
providing an indication if said velocity of said fracture fluid exceeds said threshold.

20. The method of claim 12 further comprising the steps of:
calculating an average density of said base fluid based on a plurality of density measurements of said base fluid by said Coriolis flow meter; and
determining said amount of said proppant in said fracture fluid based on said average density of said base fluid, said fracture fluid density measurement, and said density of said proppant.

21. The method of claim 12 further comprising the steps of:
measuring a mass flow rate of said fracture fluid with said Coriolis flow meter; and
providing at least one of said mass flow rate of said fracture fluid and a drive gain of said Coriolis flow meter to a user.

* * * * *

UNITED STATES PATENT AND TRADEMARK OFFICE
CERTIFICATE OF CORRECTION

PATENT NO. : 7,249,500 B2  
APPLICATION NO. : 10/542119  
DATED : July 31, 2007  
INVENTOR(S) : Robert E. Dutton and Christopher M. Russell Page 1 of 1

It is certified that error appears in the above-identified patent and that said Letters Patent is hereby corrected as shown below:

Column 8, line 34, replace "41 OR" with --410R--.

Column 12, line 3, replace "avenge" with --average--.

Signed and Sealed this

Fourth Day of December, 2007

JON W. DUDAS  
*Director of the United States Patent and Trademark Office*